Oct. 1, 1935. E. M. BARROWS Plant Pat. 143

AGROSTIS STOLONIFERA

Filed Aug. 20, 1934 2 Sheets-Sheet 1

Inventor
EARLE M. BARROWS
By Paul, Paul & Moore
ATTORNEYS

Inventor
EARLE M. BARROWS
By Paul, Paul & Moore
ATTORNEYS

UNITED STATES PATENT OFFICE

143

AGROSTIS STOLONIFERA

Earle M. Barrows, Minneapolis, Minn.

Application August 20, 1934, Serial No. 740,647

1 Claim. (Cl. 47—59)

This invention relates to a new and distinct variety of *Agrostis stolonifera*, the novel characteristics of which are its ability to produce a relatively large number of plants on a given area producing a tough resilient turf, its upright habit of growth, its freedom from graining or tropisms, its ability to withstand close cutting without injury and its ease of vegetative reproduction.

This variety originated on my residential premises at Minneapolis, Minnesota; but how and when, are unknown. Parentage is unknown. The origin was not from intentional pollination; it may have been from a planting of German mixed bent seed on my home premises 40 to 50 years ago, or from a sport of another unknown strain of bent. The characteristics herein disclosed have persisted: through eleven asexual generations covering eleven years on said premises, including at least four in shady areas and at least five under normal lawn conditions; through at least six asexual generations elsewhere covering six years, including three years at my nursery in Glendale Township, Scott County, Minn.; in one asexual generation for at least two years on a golf green at St. Paul, Minn., all propagation rights reserved by me. The variety has not been named. It was first described in print in the Greenkeepers' Reporter, vol. 2, No. 8–9, pages 1 to 8 and 18, published September 1934 at Wayzata, Minn.

This new variety of *Agrostis stolonifera* forms a turf under putting green care and conditions so closely resembling the more vigorous varieties of *Agrostis canina* as to be indistinguishable save under the most minute examination involving dissection count and measurement of individual plants making up the turf. Its color is a rather light pure green lying between the apple green and the spinach green of Koster chart of plant colors. The turf is very dense and upright in character, showing no perceptible grain nor tendency to tropisms. The leaves are slender and are involute to conduplicate. The culms are more slender than other known varieties and the turf is tough and resilient with good resistance to disease. The plants are vigorous, of rapid growth and heavily stoloniferous. The nodes bud freely making for ease of asexual reproduction and rapid production of vegetatively planted turf.

The attached drawings and specifications show the distinctions and characteristics of this variety of *Agrostis stolonifera* which has been asexually reproduced.

Figure 1:
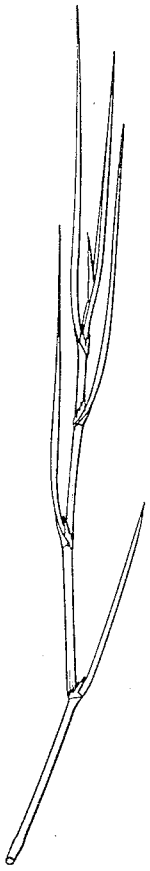
Figure 1 is a lateral view, natural size, in original drawing, of the end of a free growing stolon with its leaves showing the general nature of the angle between the leaf blade and the stem or stolon.
Figure 2:
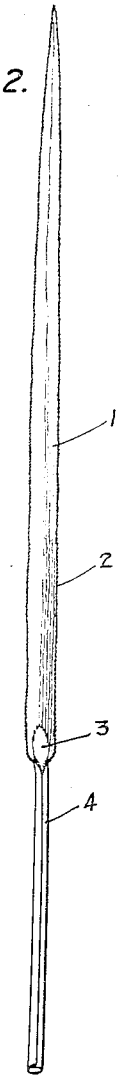
Figure 2 is a ventral drawing, magnified three diameters with respect to Figure 1, of a leaf from a free growing stolon.
Figure 3:
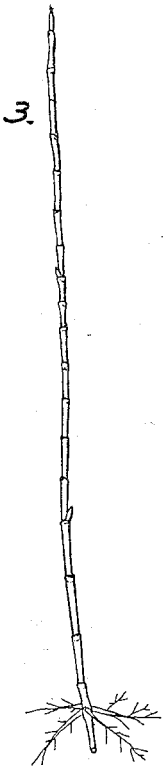
Figure 3 is an illustration of a stolon from a closely cut turf with the leaves removed showing general length of nodes, this drawing being magnified four diameters with respect to Figure 1.
Figure 4:
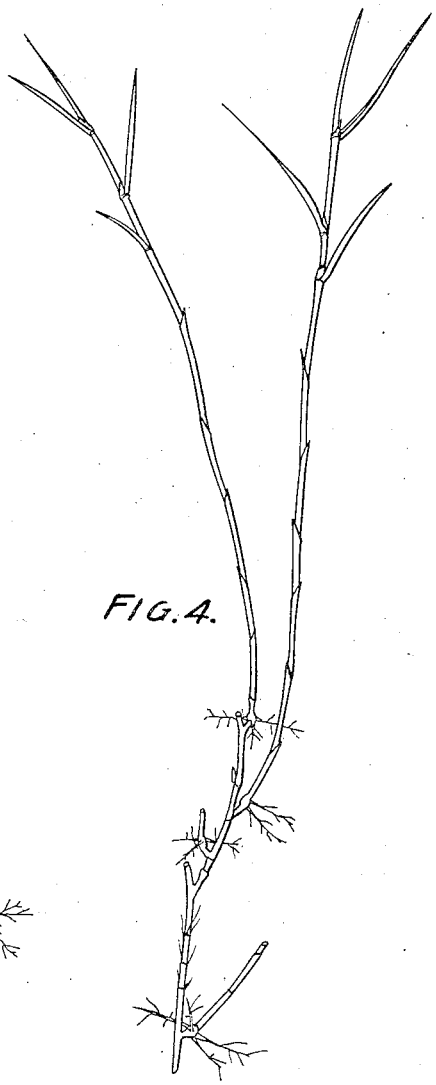
Figure 4 is an illustration magnified five diameters with respect to Figure 1 of a stolon from a closely cut turf with its leaves showing the nature of branching, with comparatively long slender stolon, small nearly straight leaves, the comparatively sharp angle between the leaf blade and the stem and the manner of rooting.
Figure 5:
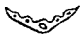
Figures 5, 6 and 7 are cross-sectional diagrams, magnified twenty diameters with respect to Figure 1, of a leaf blade from a closely cut turf, Figure 5 being a section near the tip of the leaf, Figure 6 being at about the middle and Figure 7 being a section near the base of the leaf, the said figure showing the concave upper surface of the leaf.
Figure 6:
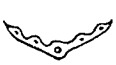
Figure 7:
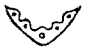
Figure 8:
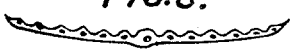
Figure 8 is a cross-sectional view, diagrammatic in character and magnified twenty diameters with respect to Figure 1 and taken near the middle of a leaf from a free growing stolon.

Referring to these drawings, particularly to Figure 2: The reference numeral 1 indicates the leaf proper and this view shows the general proportion of length of leaf blade to its width. In this same figure, reference numeral 2 indicates the scarious margin of the leaf blade; 3 is the ligule and 4 the leaf sheath or petiole.

Figure 9:
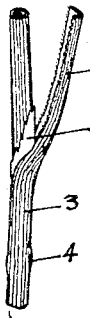
Figure 9 is a detail view, magnified five diameters with respect to Figure 1, showing the junction of a leaf blade and petiole from a section of free growing plant.
Figure 10:
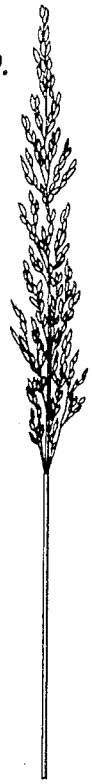
Figure 10 is an illustration of the panicle habit of this new variety, magnified two diameters with respect to Figure 1.
Figure 11:
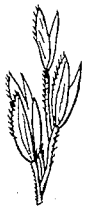
Figure 11 is an illustration of a cluster of spikelets, magnified eight diameters with respect to Figure 1.

In Figure 9, reference numeral 1 again indicates the leaf, only the base being shown; 2 indicates the ligule, 3 the leaf sheath or petiole and 4 indicates the enclosed node.

Figure 12:
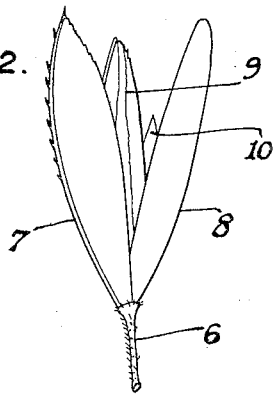
Figure 12 is an illustration of a single spikelet, magnified twenty-five diameters with respect to Figure 1.
Figure 13:
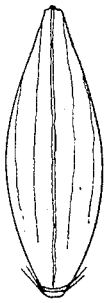
Figure 13 is a view of the dorsal side of floret showing the lemma, veins and rudimentary dorsal awn occasionally present, the view being magnified thirty diameters with respect to Figure 1.
Figure 14:
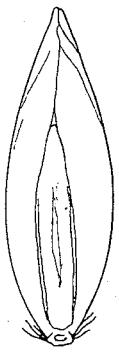
Figure 14 is a view of the ventral side of floret showing enclosed palea, attachment scar and callous bristles, the view being magnified forty diameters with respect to Figure 1.

In Figure 12, reference numeral 6 indicates the pedicel, 7 the first empty glume showing hairs in midrib and scarious hyaline margin, 8 a second empty glume, 9 a flowering glume or lemma showing the veins near the tip, and 10 is the tip of the palea.

*Free growing plants in nursery row or turf border*

The nursery rows are moderately bushy or rounded up in the centre with the tips of the marginal stolons rather flat and hugging the ground closely. The stolons are long with medium length internodes and included nodes; the leaves form an acute angle with the stem, seemingly exhibiting neutral tropisms. In this free growing state the leaves of this new variety of *Agrostis stolonifera* are very characteristic. They are long and slender with nearly parallel sides for three quarters of their length from which region they gradually taper to a point with a slight prow shape. Their average length compared with those of standard strains is as follows: New variety 5.06 cm., Metropolitan 2.8 cm., Washington, 3.875 cm., and Vermont 4.38 cm. Their average widths compare as follows: New Variety 0.24 cm., Metropolitan, 0.3 cm., Washington 0.255 cm., and Vermont 0.4 cm., making ratios of widths to length of: New Variety 1:21, Metropolitan 1:9.3, Washington 1:15.1 and Vermont 1:10.95. These measurements are the average of the three tip leaves.

The leaf blades nearly parallel the stem they are attached to and the angle between the base of the leaf blade and the culm is small and sharp. They are involute and not flat (see cross section in Figures 5 to 8), a condition that tends to hold them straight. The number of leaf veins average less than in the standard strains, the average number of veins per leaf from strains grown in the same nursery being as follows: the new strain 5 to 7; the Metropolitan 7 to 11, and the Washington 7 to 9.

The hairs at the base of the leaf are primitive, many showing only as swollen cells. The teeth on the leaf edges are irregular and poorly developed.

*In putting green turf*

Under putting green care and conditions this new variety of *Agrostis stolonifera* forms a turf having much closer resemblance to *Agrostis canina* or velvet bent than to the turf of the other known varieties of *Agrostis stolonifera*. In order to more closely define and distinguish this new variety of *Agrostis stolonifera*, an area of the sod of this new variety was established in a practise putting green in June of 1933. This green was in constant use and contained areas of the better known varieties of *Agrostis stolonifera* and of velvet bent, or *Agrostis canina*. For over a year, or until August 1934, these areas were kept under exactly the same conditions as to cutting, watering, fertilizing and top dressing. At this time plugs were cut at random from the areas of the various bents represented for purposes of comparison and identification in the putting turf form. The plugs were cut by plunging into the turf a sharpened steel tube of 1¾ inches inner diameter.

At the end of the year the turf of this new variety was upright and even in texture, showed no evidence of graining of tropisms and was very dense and resilient. The turf showed no injury from pitched balls nor could it be broken by a golf ball thrown full force directly into the surface, resembling in this respect the contiguous areas of the Metropolitan and Washington varieties of *Agrostis stolonifera*. There was no injury from large brown patch during this period though adjacent areas had mild attacks.

The leaves of the new variety in the close cut putting green turf were very slender and were markedly involute, assuming a V to U shape almost exactly resembling the leaves of the nearby patches of *Agrostis canina*, the leaves of the latter being a trifle more slender but of the same shape and general appearance.

The following counts and measurements were taken from the plugs cut at random, as before mentioned, each circular plug having a uniform diameter of 1¾ inches, an area of approximately 2.4 square inches. While different soil and climatic conditions would probably produce different totals, the relative values would remain the same and afford an accurate means of identification.

The first table shows the number of complete plants counting only plants having roots, stems and leaves. The numbers at the top represent the number of branches on each plant. For example, the numeral 1 represents the number of complete plants having no branches; 2, those having two branches, etc., the total number of branches representing the number of culms composing the putting surface of the green and is directly representative of the relative density of the turf.

| | Number of branches to each plant | | | | | | | | | Totals | |
|---|---|---|---|---|---|---|---|---|---|---|---|
| | 1 | 2 | 3 | 4 | 5 | 6 | 7 | 8 | 9 | *Plants* | *Branches* |
| New variety | 142 | 63 | 21 | 6 | 7 | 2 | ---- | ---- | ---- | 241 | 402 |
| Velvet | 186 | 68 | 16 | 9 | 4 | ---- | ---- | ---- | 1 | 284 | 435 |
| Metropolitan | 160 | 44 | 16 | 3 | 4 | 1 | ---- | ---- | ---- | 228 | 334 |
| Vermont | 78 | 34 | 21 | 9 | 1 | 1 | ---- | ---- | ---- | 144 | 256 |
| Washington | 103 | 45 | 13 | 6 | 5 | ---- | ---- | ---- | ---- | 172 | 281 |

The diameter of a number of stems or culms taken from the various strains grown on this same practise putting green under precisely the same conditions was as follows: (It will be noted that the average diameters follow closely the relative density as show in the preceding table).

*Average diameters of stolons in putting green turf taken immediately below the third leaf from the tip*

| | New variety | Metropolitan | Vermont | Washington | Velvet |
|---|---|---|---|---|---|
| Diameter | 0.228 mm. | 0.315 mm. | 0.362 mm. | 0.278 mm. | 0.168 mm. |

In this putting green the leaves of this new variety of *Agrostis stolonifera* had 3–5 veins, the Metropolitan 5–7, Washington 7–9 and Vermont 9–11 veins, following again the relative density. In turf the leaves again have a much smaller angle between their blades and their culms, producing an upright growth. In this case the leaves are decidedly involute and straight, rather than flat and curved back as especially typified in Metropolitan.

*The plant under lawn care*

The turf formed by this new variety of *Agrostis stolonifera* when cut and cared for in lawn form, that is, cut once a week, at ½ inch height and not topdressed, maintains in general its comparative characteristics as to density and measurements with the other varieties. This new variety maintained an upright and very dense turf formed of fine culms without matting or running. The Vermont also maintained a true turf though very thin in comparison. The Metropolitan and Washington, however, form a flat matted growth with marked grain, the growth being a mat of shortened stolons rather than a true turf.

Although herein are stated the general characteristics of this new variety of *Agrostis stolonifera* it is understood they may vary slightly due to soil or climatic conditions.

I claim as my invention or discovery:

A distinct and new variety of *Agrostis stolonifera* as herein shown and described, characterized by its ability to produce a very large number of plants per given area, forming a tough and resilient turf of great density; its slender leaves, involute to con-duplicate in form; its slender culms; its upright habit of growth in turf form; its freedom from tendency to become grainy or fluffy in turf form; its ability to withstand close mowing without injury; its high resistance to disease; its hardiness; and its ease of vegetative reproduction.

EARLE M. BARROWS.